United States Patent [19]

Guiseppi-Elie

[11] Patent Number: 5,352,574
[45] Date of Patent: Oct. 4, 1994

[54] SURFACE FUNCTIONALIZED AND DERIVATIZED ELECTROACTIVE POLYMERS WITH IMMOBILIZED ACTIVE MOIETIES

[76] Inventor: Anthony Guiseppi-Elie, 1017 Randolph Dr., Yardley, Pa. 19067

[21] Appl. No.: 771,759

[22] Filed: Oct. 4, 1991

Related U.S. Application Data

[63] Continuation of Ser. No. 322,670, Mar. 13, 1989, abandoned.

[51] Int. Cl.$^5$ .......................... C12Q 1/00; C12Q 1/26; C12N 11/08; G01N 33/545
[52] U.S. Cl. ........................................ 435/4; 204/403; 435/25; 435/180; 435/181; 435/817; 436/531; 436/532
[58] Field of Search .................. 435/4, 25, 174, 177, 435/180, 181, 817; 204/403; 436/531, 532

[56] References Cited

U.S. PATENT DOCUMENTS

| | | | |
|---|---|---|---|
| 4,352,884 | 6/1982 | Nakashima et al. | 435/180 |
| 4,371,612 | 2/1983 | Matsumoto et al. | 435/180 X |
| 4,622,362 | 11/1986 | Rembaum | 435/180 X |
| 4,721,601 | 1/1988 | Wrighton et al. | 422/68 |
| 4,839,017 | 6/1989 | Taniguchi et al. | 435/817 X |

*Primary Examiner*—David M. Naff
*Attorney, Agent, or Firm*—Synnestvedt & Lechner

[57] ABSTRACT

New variants of electroactive and optoactive polymers are formed from the surface chemical modification and derivization of free-standing and substrate-supported polymer films. The free-standing or substrate-supported films are chemically modified at or near their surfaces to introduce hydrophilic and/or reactive functional groups, such as carboxylic acids, hydroxyls, and amines. Surface derivatization of the modified polymer film is achieved through the specific attachment of bioactive, immunoactive, electroactive, and catalytic agents to the surface of the electroactive or optoactive polymer film. In one embodiment, a polymer selected from polyacetylene, polypyrrole, polyanilane and polythiophene is modified to contain functional groups and an indicator reagent is covalently coupled to the functional groups. When an analyte in a sample reacts with the indicator reagent, electrical conductivity of the polymer is changed and presence of the analyte is indicated by the change in electrical conductivity.

11 Claims, 4 Drawing Sheets

FAD / FLAVIN ADENINE DINUCLEOTIDE

SURFACE FUNCTIONALIZED AND DERIVATIZED ELECTROACTIVE POLYMERS WITH IMMOBILIZED ACTIVE MOIETIES

This application is a continuation of co-pending U.S. Ser. No. 322,670 filed Mar. 13, 1989, now abandoned.

BACKGROUND OF THE INVENTION

This invention relates to new variants of electroactive and optoactive polymers formed by the surface chemical modification and derivatization of free-standing and substrate-supported polymer films as well as processes for their formation.

Polyacetylene has been known for some considerable time since its first synthesis by Natta et al. as a black, intractable powder in 1958. See Natta et al., 25 *Atti, Acad. Nazl. Linci. Rend, Classe Sci, Fis, Mat.* 3 (1958). However, this material has only attracted wide basic and applied research interest since its first reported synthesis as a lustrous, free-standing, polycrystalline film by Shirakawa et al. in the early seventies. See Shirakawa et al., 2 *Polym, J.* 231 (1971); Shirakawa et al., 4 *Polym, J.* 460 (1973); Ito et al., 12 *J. Polym, Sci,; Polym, Chem, Ed.* 11 (1974); and Ito et al., 13 *J. Polym, Sci,; Polym, Chem, Ed.* 1943 (1975). Equally important has been the subsequent discovery by MacDiarmid et al. in 1978 that the material could be made to alter its intrinsic electrical conductivity when exposed to various redox-active agents erroneously called "dopants", and that the resulting conductivities could be made to approach that of pure metals. See U.S. Pat. No. 4,222,903 issued to Heeger et al. on Sep. 16, 1980. It has now been demonstrated that polyacetylene can be made to alter its intrinsic electrical conductivity through both chemical redos processes and electrochemical redos reactions. (See Diaz et al., 111 *J. Electroanal. Chem.* 115 (1980); MacDiarmid et al., 105 Mol. Cryst. Lig, Cryst. 89 (1984)).

Redox processes which lead to charge (electron) transfer from the pristine polymer, i.e. oxidation, give rise to p-type electrical conductivity and redox processes which lead to charge transfer to the pristine polymer, i.e. reduction, give rise to n-type electrical conductivity. In this way, polyacetylene can be made to alter its electrical conductivity from its insulating as-synthesized state, (conductivity of $10^{-9}$ ohm$^{-1}$ cm$^{-1}$), through a semiconducting state, onto a metallic state (conductivity of $10^3$ ohm$^{-1}$ cm$^{-1}$) through 12 orders of magnitude. This 12 orders of magnitude change in conductivity is achieved for a change in the redos state of 1 to 3 mole percent of available redox active moieties within the polymer.

The availability of polyacetylene in film form and its unusual electrical conductivity has stimulated considerable fundamental and applied science interest in this polymer. Foremost among these are interest in reversible storage batteries (Macinnes, Jr. et al., 3 *J. C. S. Chem. Commun.* 317 (1981), electronic devices, photoelectrochemical solar cells, and analytical devices (U.S. Pat. No. 4,444,892 issued to Malmros on Apr. 24, 1984).

Unfortunately, polyacetylene suffers from a number of major technological limitations. The pristine material is unstable in ambient temperatures and is very reactive with oxygen, becoming embrittled and undopable. The polymer is also inherently reactive with some of the counter ions which are formed as a consequence of charge transfer doping reactions. This reactivity leads to a precipitous loss of conductivity over time and on the order of days. Additionally, the polymer is intractable and cannot be processed by conventional methods. U.S. Pat. No. 4,499,007 issued to Guiseppi-Elie et al. on Feb. 12, 1985 addresses the issue of stability and provides a method for the stabilization of the polymer in aqueous environments.

Prior art techniques for addressing many of the fundamental limitations of polyacetylene have focused on methods of synthesis of new variants of the polymer. For example, U.S. Pat. No. 4,394,304 issued to Wnek on Jul. 19, 1983 discloses a method for forming a conductive polymer by the in situ polymerization of acetylene within a matrix of a more processable polymer. A similar and related approach is described in U.S. Pat. Nos. 4,510,075, 4,510,076, 4,616,067, 4,705,645 issued to Lee et al., in which acetylene is synthesized in a matrix of a more processable polymer which possesses low unsaturation and is accordingly cross-linkable via Cobalt 60 Gamma-radiation and in various tri-block copolymers. Another approach is that disclosed by Widdegen in U.S. Pat. No. 4,444,970 in which a substituted polyacetylene is formed from the synthesis of regular acetylene monomer in the presence of a substituted acetylene monomer.

The surface of pristine and semiconducting, as well as doped and metallic, free-standing, polyacetylene film has been investigated by Guiseppi-Elie et al., 2 *Landmuir* 508 (1986). In this work it is demonstrated that the surface of pristine, semiconducting polyacetylene film was hydrophobic with a critical surface tension for wetting of 40.1 mN m$^{-1}$ and a dispersion component of surface energy of 58 mN m$^{-1}$.

In other related work, Guiseppi-Elie et al., 23 *J, Polym, Sci,; Polym, Chem, Ed.* 2601 (1985) also demonstrated the surface chemical modification of free-standing polyacetylene film for the introduction of hydrophilic functional groups. In this work the double bonds of the polyacetylene backbone, which are at the near surface, were oxidized using wet chemical oxidative techniques. The result of the surface chemical modification was to alter the energetics of the surface by the introduction of reactive, hydrophilic, surface hydroxyl functional groups. Specifically, Guiseppi-Elie et al. used a method based on permanganate oxidation of surface double-bonds to introduce surface hydroxyl groups to the near surface of preformed polyacetylene film. Using this method, a 30 second treatment in the permanganate solution changed the contact angle made by water at the polyacetylene surface from 72° to 12°.

However, in the context of polyacetylene, the consequence of such compositional changes typically is an appreciable sacrifice of electrical conductivity for only modest improvements in stability and processability.

In many technological applications of surfaces there is a need to achieve a topologically uniform, ultra thin organic overlayer of controlled and uniform surface chemistry. Moreover, it is desirable to introduce via adsorption or through specific immobilization, various other molecules which are different in function and purpose to the underlying substrate layer. These overlayer molecules will then confer to the substrate solid the physicochemical properties of the overlayer. Additionally, the overlayer may interact with the substrate underlayer so as to produce some new overall effect, phenomena, or materials property. Such complex, composite, layered structures are called supramacromolecular assemblies.

Of particular importance in such structures are chemical and biological sensors formed from the immobilization of bioactive and catalytic species to the surface of a polymer such as polyacetylene. Polyacetylene is well known to change its electrical conductivity though 12 orders of magnitude upon exposure to, inhibition of, and reaction with, various small redox-active molecules commonly called dopants. Examples of such dopants include ferric chloride, iodine, bromine, and hydrogen peroxide. Polyacetylene used as a sensor in this free-standing film configuration, however, suffers from a major limitation in that its response to environmental redox-active agents is non-specific. That is, any redox active small molecule of appropriate redox potential will induce a change in the polymer. It is extremely desirable to confer reaction specificity and sensitivity of response to polyacetylene films when exposed to these redox active agents.

SUMMARY OF THE INVENTION

New variants of electroactive and optoactive polymers, formed from the surface chemical modification and derivization of free-standing and substrate-supported polymer films, and processes for the production of these new variants, are disclosed. The free-standing or substrate-supported films are chemically modified at or near their surfaces introduce hydrophilic and/or reactive functional groups, such as carboxylic acids, hydroxyls, and amines. Oxidative and wet chemical techniques for such surface chemical modification of polymers are also disclosed. Surface derivatization of the modified polymer film is achieved through the specific attachment of bioactive, immunoactive, electroactive, and catalytic agents to the surface the electroactive or optoactive polymer film.

In one aspect of the invention a process is provided for the specific (i.e., involving covalent bond formation rather than adsorption) immobilization of an indicator reagent upon a surface of an electroactive or optoactive polymer film. In this process a chemically modified electroactive or optoactive polymer film surface is reacted with a linking agent and then the linking agent is reacted with an indicator reagent so that it is bound to the surface of the substrate via covalent bond formation.

Another aspect of the invention is to provide a sensor for detecting the presence of an analyte using an electroactive or optoactive polymeric substrate having a surface derivatized with an indicator reagent which reacts in the presence of the analyte wherein the analyte modifies the electrical or optical properties of the substrate.

Still another aspect of the invention is to provide an analyzing system for detecting the presence of an analyte by using an electroactive or optoactive polymeric substrate and an indicator reagent derivatized to the surface of the substrate which reacts in the presence of the analyte, wherein the analyte modifies the electrical or optical properties of the substrate.

A further aspect of the invention is provide a method of detecting the presence of analyte in a sample by contacting the sample with polymeric substrate having a surface derivatized with an indicator reagent which reacts in the presence of the analyte wherein the analyte modifies the properties of the substrate.

In a further aspect of the invention, a process is provided for the chemical modification of the surface of polyanilane films by reacting the surface with reagents which result in the occurrence of hydrophilic and reactive functional groups on the surface of the film and thereby produce an activitated surface through which can be linked an immobilized molecule.

Another further aspect of the invention is chemically modified polyaniline films with activated surfaces, through which can be linked an immobilized molecule.

The term "electroactive" is used herein to encompass a variety of polymeric substrates, having electrical activity, conductivity, capacitance or the like. Similarly, the term "optoactivity" is used herein to encompass polymeric substrates having optical activity, color, transmissivity, absorptivity, reflectance or the like.

The present invention will next be described in connection with certain illustrated embodiments. However, it should be clear that various additions, subtractions and modifications can be made by those skilled in the art without departing from the spirit or the scope of the invention.

BRIEF DESCRIPTION OF THE DRAWINGS

The foregoing and other objects of this invention, the various features thereof, as well as the invention itself may be more fully understood from the following description, when read together with the accompanying drawings, in which.

DETAILED DESCRIPTION

This invention relates to new variants of polymers and methods for their formation. This invention also relates to new supramacromolecular organic structures which are formed from the specific attachment of an organic overlayer onto previously surface chemically modified, free-standing and substrate-supported, semi-conducting, polymer films. The polymer films are formed by the post-fabrication reaction of the free-standing or substrate-supported film with chemical agents designed to convert the high unsaturation at or near the surface into reactive, polar functional groups such as hydroxyls, carboxylic acids, amines, or sulphonates, etc. These new functional groups render the film hydrophilic and reactive. These hydrophilic and reactive functional groups then serve as the sites for the specific attachment of bioactive, immunoactive, electroactive, and optoactive moieties to the surface of the free-standing or substrate-supported polymer film. The surface chemical modification and the subsequent surface immobilization of other organic moieties to achieve the supramacromolecular complex are to be carried out after synthesis of the free-standing or substrate-supported film.

Reactive, surface functional groups which are formed at the near surface of preformed, free-standing polyacetylene films are used to build supramacromolecular structures in which bioactive, redoxactive moieties, and other moieties are specifically attached to the surface of the chemically modified, preformed polyacetylene film. In this way the polyacetylene film is derivatized and new variants of polyacetylene are formed.

Figure 1:
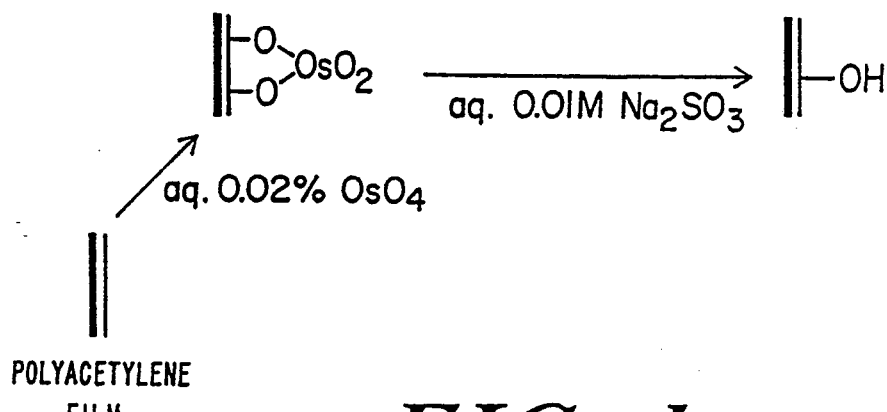
FIG. 1 is a schematic illustration of a process for the surface modification of a polyacetylene film according to the invention.

FIG. 1 shows schematically the chemistry of surface modification of the free-standing, preformed polyacetylene film according to example 3. This method uses aqueous $OsO_4$ oxidation followed by sulphite hydrolysis to yield the desired di-alcohol product. It can be seen in this example that the purely hydrophobic, hydrocarbon surface of the polymer is made to react with osmium tetroxide at olefinic sites. This reaction is carried out preferably at room temperature and in aqueous solution in which the osmium tetroxide concentration is around 0.02%. This reaction generates the labile osmate ester. The ester is subsequently hydrolysed in dilute sodium sulphite to give the syn-diol product. This reaction is not accompanied by measurable changes in the electrical conductivity of the base polymer. Fourier transform attenuated total reflectance IR spectroscopy confirms no charge-transfer "doping" of the polymer as there is no evidence of the infrared active band at 1400 $cm^{-1}$ associated with carbocation formation.

Figure 2:
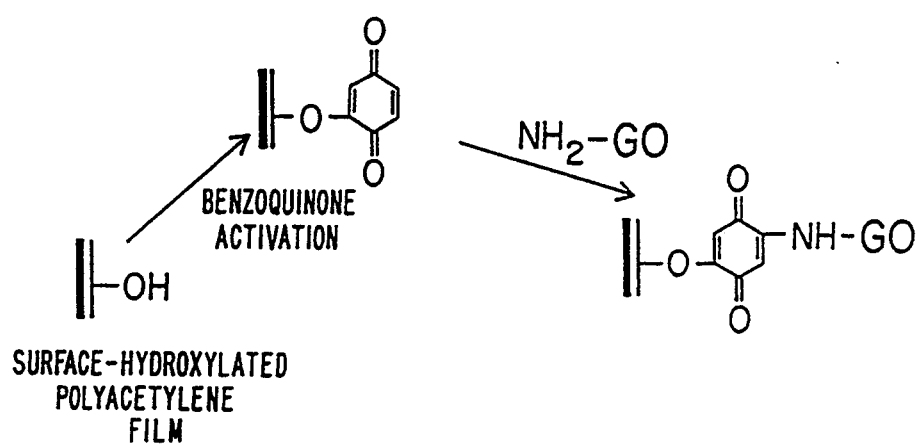
FIG. 2 is a further schematic illustration of a reaction of a linking agent with a surface modified polyacetylene film and the subsequent immobilization of an enzyme on the surface modified polyacetylene film in accordance with the invention.

FIG. 2 shows schematically the supramacromolecular complex formed from the specific immobilization of the enzyme glucose oxidase to the surface of chemically modified, free-standing, preformed polyacetylene film according to example 4. This reaction proceeds in two steps. Firstly, there is activation of the hydroxyl bearing surface with benzoquinone to yield a quinone functionalized surface. This reaction occurs at room temperature in a saturated solution of benzoquinone prepared in a mixed solvent medium of anhydrous 1% isopropyl alcohol in absolute ethanol. The quinone bearing surface is then allowed to react with an aqueous solution of the enzyme glucose oxidase prepared in pH=7.2 phosphate buffered saline. This reaction results in enzyme immobilization at the previously hydroxylated polymer surface.

The surface derivatized films of this invention have the advantages of: providing a topologically conformal, chemically homogeneous, fully anchored film of the immobilized chemical agent; displaying enchanced specificity of response, if active, to environmental, chemical, and biological agents; and the building of a supramacromolecular complex.

The surface derivatized films disclosed herein show improved wettability when in contact with aqueous environments. Also such films, due to their covalently immobilized entities, have technologically significant properties such as: biospecificity imparted by immobilized enzymes, antibodies, and hormones; catalytic properties imparted by covalently immobilized organic and inorganic catalysts; and redox mediation properties imparted by the covalent attachment of radox active mediators such as ferrocene and enzyme cofactors.

In addition, such films show increased sensitivity in their electrical conductivity, electrode potential, redox potential, dielectric constant, ionic conductivity, electrochromic responses and other materials properties responses to the products of the reaction of the immobilized entities.

Electroactive polymers such as polyacetylene, polypyrrole, polyaniline, and others, have been discovered to potentially serve as the transducer-active materials in various sensor devices.

In addition to its electrical properties, polyaniline can be viewed as an optoactive polymer since it is photochromic. Therefore, optical properties of polyaniline, such as optical absorption coefficient and color can be modulated and form the bases for a measurement system.

Polyacetylene can be made to react with oxidants and reductants and to alter its conductivity proportionately with the amount of reductant or oxidant so reacted. If a constant voltage is maintained across a fixed dimension of the polymer film, then an electrical current can be found to exist in the film, the magnitude of which is a measure of its electrical conductivity. If an appropriate reductant or oxidant was to be brought into contact with the film, then there will be found a change in the magnitude of the current existing in the film. The change in magnitude of the current will reflect changes in the composition of the film resulting from reactions of the reducing or oxidizing agent therewith and to bear a definable, reproducible relationship one with the other.

In this respect, the polymer transmutes the chemical potential associated with the amount reactable redox species into an electrically based signal and does so directly. Such a material described here, for the first time, as being transducer-active. Transducer-active materials form the basis for the fabrication of chemical and biological sensor devices.

A clear problem in the application of transducer-active polyacetylene film to chemical and biological sensors, is the inability of the transducer-active polymer film to discriminate, i.e. respond selectively to those redox-active species, the chemical potential of which we desire to be measured, and those which are ubiquitous to the measuring environment. This problem, redefined, is one of conferring specificity of action to the transducer-action of the electroactive polymer film. The solution to this problem is to confer to the transducer-active polymer film the chemical and biological specificity required for such discrimination.

A high degree of specificity is achieved by exploiting two phenomena; the first is called the "proximity effect" and the second is the chemical and biological specificity associated with catalysts;, enzymes, and mono and polyclonal antibodies. The proximity effect restated, is a shortening of the diffusion part to the transducer-active film for one reagent-the desired reagent or analyte, over all others in the measurement environment. This is achieved by the specific immobilization of the chemical or biological catalysts at the surface of the transducer-active polymer film. Enzymes, being organic, biological, catalysts, are examples in point. Enzymes are substrate-specific and accordingly will display large preferences for reaction with one chemical substance, its substrate, over another (a non-substrate). This high degree of specificity of action is what is desired in the action of transducer-active, polymer film. This result is achieved by specifically attaching, through covalent bond formation, the enzyme to the surface of the polymer film. The result is a "composite" film which possesses the desirable properties of both types of material and also exploits the proximity effect.

Among those oxidants that will induce conductivity changes in a polymer such as polyacetylene is the oxidant hydrogen peroxide. A dilute, aqueous solution of hydrogen peroxide, when brought into contact with a strip of polyacetylene film, will react with the polyacetylene film to measurably alter its electrical conductivity. Indeed, a calibration curve of conductivity change (response) versus hydrogen peroxide concentration (dose) can be readily prepared.

The enzyme glucose oxidase is one of those cofactor based enzymes which produces hydrogen peroxide as a consequence of glucose oxidation. The rate of hydrogen peroxide production by the enzyme is, to a first approximation, directly proportional to the amount of glucose available. When the enzyme is immobilized at the surface of the transduceractive polyacetylene film, the hydrogen peroxide produced as a result of glucose oxidase activity is in intimate proximity to the polyacetylene film substrate and reacts directly with the film.

By immobilizing the enzyme glucose oxidase to the surface of the polymer film, the following two important things are achieved.

First, reactivity of the film is conferred to an agent (glucose) with which it is usually not reactive—albeit indirectly, through its direct reaction with a signature product of glucose/enzyme reaction—hydrogen peroxide. Second, the hydrogen peroxide produced is in intimate and direct contact with the transducer active film, thereby reducing its diffusion pathway for reaction with the film.

The composite or derivatized polyacetyiene film is the basis for a wide range of biosensors which find application in diagnostics, environmental monitoring, and in process control.

The invention will be further understood from the following non-limiting examples.

EXAMPLE 1

Synthesis Of Free-standing, Polycrystalline, Polyacetylene Film

Free-standing, polycrystalline, cis-polyacetylene film was synthesized using a modification of the published method of Shirakawa et al. See Shirakawa et al., 2 *Polym, J.,* 231 (1971); Shirakawa et al., 4 *Polym, J.,* 460 (1973); Ito et al., 12 *J, Polym, Sci,; Polym, Chem, Ed.,* 11 (1974); and Ito et al., 13 *J, Polym, Sci,; Polym, Chem, Ed.* 1943 (1975). In this method polyacetylene is prepared by the polymerization of acetylene monomer using a Ziegler-Natta catalyst solution. The Ziegler-Natta catalyst was prepared from previously distilled titanium tetrabutoxide (Alpha) and as-supplied triethyl aluminum (Ethyl) in a large Schlenk flask. Using a 5 ml glass syringe fitted with a 16 gauge stainless steel needle, 1.7 ml of the viscous, pale yellow titanium tetrabutoxide was transferred from its storage under argon to the Schlenk flask containing 20 ml of freshly distilled toluene held at dry-ice/acetone temperature (−78° C). The contents of the flask was maintained under a bleed stream of argon during transfer. Using a similar 5 ml syringe fitted with a 18 gauge stainless steel needle, 27 ml of triethyl aluminum was transferred to the contents of the Schlenk flask. The result was an active catalyst mixture in a 1:4 Ti:Al mole ratio and at a concentration which was 0.2 molar with respect to titanium tetrabutoxide. The catalyst solution was aged at room temperature for ca. half hour following preparation, then cooled again to −78° C. and subjected to brief evacuation by dynamic vacuum. In a separate step, high purity grade acetylene (Mattson) was further purified by slowly bubbling the gas through a serial train comprising two reservoirs of concentrated sulphuric acid, a U-tube containing phosphorous pentoxide, and finally over a bed of 2 Angstrom molecular sieves. The gas was stored in a 1 litre all glass reservoir until synthesis. The cold and now viscous catalyst solution was shaken onto the glass walls of the Schlenk flask and allowed to drain slowly. To the quiescent but draining surface of the catalyst solution was introduced the ca. 1 litre of purified acetylene gas. The highly purified acetylene was introduced into the reaction chamber at pressures which ranged from 700 to 750 mm Hg. Rapid polymerization of the acetylene occurred by growth the polymer on the surface of the catalyst solution.

The cohesive film grows on the surface of the quiescent catalyst within a few seconds, or up to 1 hour, depending on the pressure and temperature employed. The film was punctured and the spent catalyst beneath was removed using a syringe and needle. The film was then washed repeatedly in distilled toluene, followed by pentane and finally by ethanolic hydrochloric acid until there was no visible evidence of the catalyst solution. The Schlenk flask reactor was transferred to a nitrogen glove box where the polyacetylene films were cut into strips and stored under reduced pressure following a backflush with argon and maintained in this condition until used in subsequent steps. Films may be stored in this condition for upwards of 6 years with no obvious change in appearance. The polyacetylene films prepared in this way have a lustrous silvery appearance and are quite flexible. Films varying in thickness from 0.1 mm to 0.5 mm or more can be made, depending on time and catalyst concentration used in the synthesis.

EXAMPLE 2

Synthesis Of Free-Standing, Polycrystalline, Polyacetylene Film

Free-standing polyacetylene films were synthesized as demonstrated in Example 1 above, however the catalyst solution was prepared by transfer of titanium tetrabutoxide and triethylaluminum into a solution of 10 wt/0 Kraton 1107 (styrene-isoprene-styrene tri-block co-polymer) (Shell Chemical Co.) in toluene and reacted at room temperature. The resulting polymer was shown by attenuated total reflectance IR spectroscopy to possess IR active bands consistent with the identity of the tri-block copolymer. Room temperature solvent extraction of the film in toluene revealed a weight change of ca. 4% after three-days.

EXAMPLE 3

Introduction Of Surface Hydroxyls Using Aqueous Osmium Tetroxide

Dilute aqueous solutions of 0.02% osmium tetroxide were prepared from 1:10 v/v dilution of stock ampules of 0.2% aqueous osmium tetroxide solution (Polysciences Corporation). Solutions were prepared under an argon atmosphere in a disposable glove bag ($I^2R$) stationed in a fume hood. The freshly prepared solution was degassed by bubbling with prepurified argon (Arco). Polyacetylene film strips, prepared according to Example 1 and 2, were transferred to the glove bag, removed from storage, and cut into pieces 2×4 cm in the glove bag. These film strips were immersed in the osmium tetroxide solution for varying periods of time at room temperature. Each film strip was subsequently removed after its allotted time of reaction of 0.5, 1, 3, 5, 10, and 30 minutes, then rinsed profusely in deionized, distilled water. The films were then dried for no less than 48 hours in a desiccator which was kept at room temperature and under argon. The film strips were subsequently mounted, smooth surfaces up, onto glass microscope slides using double-sided Scotch(TM) Tape. The contact angle made by water on the chemically treated smooth surface and on the smooth surface of untreated reference film was subsequently measured using a Rame Hart Contact Angle Goniometer. The contact angle at the chemically treated surface was found in all cases to be ca. 55 degrees while the untreated surface was measured at 72°±5° C. In another sequence of experiments, the film strips were transferred to and immersed in a gently stirred, diluted solution (0.01 M) of aqueous sodium sulphite ($Na_2SO_3$) prior to the desiccation step. The films were submerged for a period of 1 minute, removed, then rinsed profusely in distilled, deionized water. Like before, the film strips were dried at room temperature in a desiccator under prepurified argon for no less than 48 hours. The contact angle of water measured on these films were in all cases less than 10 degrees. The reaction of osmium tetroxide with the olefinic double bonds is known to give rise to the osmate ester (J. March, Advanced Organic Chemistry 748 (2d ed. 1977)), which on subsequent hydrolysis leaves the di-alcohols at the surface as shown in the reaction scheme of FIG. 1.

EXAMPLE 4

Specific Immobilization Of The Enzyme Glucose Oxidase To The Surface Of The Chemically Modified Polyacetylene Film The surface hydroxyl functionalities produced by the above procedures (according to example 3) were made to react with benzoquinone which serves as a linking agent for the specific immobilization for the enzyme glucose oxidase. A saturated solution of p-benzoquinone (Aldrich Chemical Co.) was freshly prepared in anhydrous 1% isopropyl alcohol in absolute ethanol. Polyacetylene film strips, prepared according to Example 1 and 2, were removed from storage, cut into pieces 2×3 cm and chemically modified according to procedures outlined in Example 3 above. The chemically modified film strips, bearing hydroxyl functionalities at the near surface, were immersed in the benzoquinone solution. After ca. 30 minutes of immersion, the film strips were removed, rinsed in deionized, distilled water then immediately transferred to a cold, pH 7.2, phosphate-buffered saline solution of glucose oxidase (Type VII-S; EC 1.1.3.4 from *Aspergillus niger*; 129,000 units of activity per gram of solid) (Sigma Chemical Co.). The film strips were allowed to be incubated overnight in the glucose oxidase solution in a sealed container in a refrigerator at 5° C. Benzoquinone is well known to cause chemical activation of hydroxyl containing surfaces (Brandt et al., 386 *Biochim, Biophys, Acta* 196 (1976) through formation of the hydroxy quinone. The surface confined hydroxy quinone then acts as an effective linking agent between the activated surface and enzyme molecules (Narasimhan et al., 7*Enzyme Microb, Techno.* 283 (1985). Benzoquinone is also known to induce charge transfer reactions with polyacetylene leading to "doping" and modest conductivity changes.

Following overnight incubation, the film strips were removed and tested for immobilized enzyme activity using a procedure reported by Wingard, Jr. et al., 748 *Biochim, and Biophys, Acta* 21 (1983). Unmodified control film strips were found to have around 0.8 munits of activity per sq. cm, while functionalized and activated film strips were found to have around 75 munits of activity per sq. cm. showing clear activation and immobilization of the enzyme at the surface of polyacetylene as illustrated in FIG. 2.

EXAMPLE 5

Figure 3:
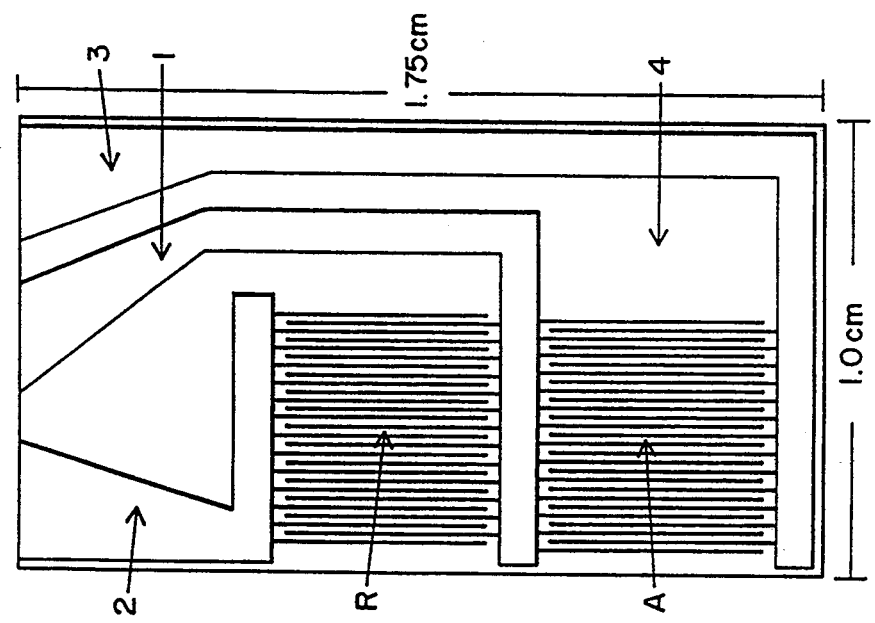
FIG. 3 is a top view of a sensor employing an analyzing system in accordance with the invention.

Oxidative Electrosynthesis Of Polyaniline Film On An Interdigitated Microelectrode Array Polyaniline was synthesized from aniline monomer at interdigitated, gold, microelectrodes using a modification of the established electrochemical procedures first reported by Diaz et al., 111 *J, Electroanal, Chem.* 111 (1980) and subsequently outlined by Focke et al. in 91 *J. Phys. Chem.* 5813 (1987). FIG. 3 shows schematically a microelectrode array comprising a common electrode 1, a reference electrode 2, an analyte electrode 3, interdigitated electrode grid areas A and R, and an insulating electrode support 4. These electrodes are gold microelectrodes formed as an interdigitated microelectrode array on an insulating quartz substrate. The gold electrode patterns were formed by magnetron sputtering of approximately 1,000 Å chromium (Cr) followed by approximately 300Å of gold (Au). The metallization was then resist patterned and developed to yield a combined differential (CD), two-probe, interdigitated microelectrode array of 15 micron line and space dimensions and containing 50 finger pairs. Before electrosynthesis, the electrodes were rinsed in degreasing solvent and cathodically cleaned by repeated cycling between −1.2 V to −0.2 V vs the saturated calomel reference electrode (S.C.E.) in pH 7.2 phosphate buffered saline.

Pale yellow liquid aniline (Aldrich) was distilled under reduced pressure to yield a clear, colorless, solution. A 100 ml aliquot of the working solution was prepared by mixing 10 ml of distilled aniline in 90 ml of 2.0 molar Analar Hydrochloric Acid (Aldrich). The resulting solution was ca. 1 molar in aniline. The interdigitated gold microelectrode was introduced into 3 ml of the working solution in a specially constructed electrochemical cell which was fitted with a Saturated Calomel Electrode via a Luggin Capillary and a platinized, platinum ribbon counter-electrode. The cell was deaerated for ca. 15 minutes with prepurified argon before commencing electrosynthesis.

Both leads of the interdigitated, gold, microelectrode were repeatedly cycled between −0.2 V to +0.65 V vs S.C.E. in the ca. 1 molar aniline working solution. The film was observed to grow with repeated cycling for up to 5 hours under these conditions to yield a green fully adherent, contiguous film. The film bearing electrode was then isolated and washed repeatedly with 1 molar HCl.

Figure 4:
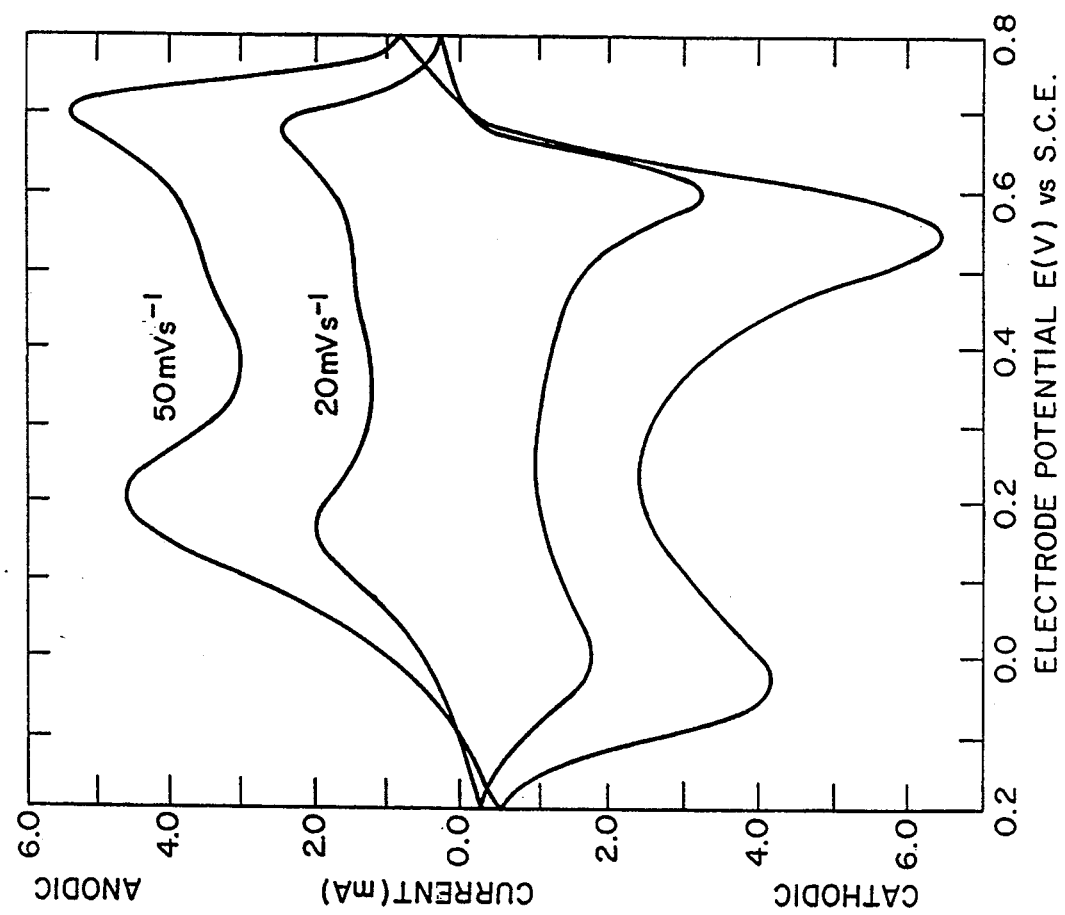
FIG. 4 is a graph showing the redox activity for polyaniline deposited on the sensor of FIG. 3.

The resulting film displayed the characteristic redox activity established for polyaniline shown in FIG. 4.

The array of FIG. 3 with its polymeric film coating can be used as a sensor in the analytical systems of the present invention to detect the presence of an analyte. In such applications, the surface of the polymeric film overlying the interdigitated grid area A is derivatized with an indicator reagent which will react in the presence of the analyte to modify the electrical properties of the film overlying grid area A.

The sensor can then be deployed to measure an unknown concentration of an analyte in a sample (e.g., via immersion in a liquid sample or exposure to a gaseous sample). By comparing the electrical response sensed on the analyte electrode 3 (measuring the electrical properties of grid area A) with that sensed on electrode 2 (measuring the electrical properties of grid area R), differences in the electrical responses can be correlated with analyte concentration in the sample.

EXAMPLE 6

Oxidative Electrosynthesis Of Polyaniline Copolymer Films On Interdigitated Microelectrode Array Copolymer synthesis was achieved under conditions similar to those described in Example 5 above. To produce the desired copolymer product, the composition of the film forming solution was varied accordingly to include an appropriate mole faction of the co-monomer. A working solution was prepared from 1.5 ml of 1 molar aniline in 2.0 molar HCl and 1.5 ml of saturated 3-amino-4-methyl-benzoic acid in 2.0 molar HCl. The result was a working solution which was 0.5 molar in aniline and of unknown concentration of 3-amino-4-methyl-benzoic acid. Other polymerizable monomers were used in a similar mannnet and were drawn from the list shown in Table 1. Each co-monomer was prepared as a room temperature saturated solution in 2 molar hydrochloric acid as described for aniline in Example 5 above.

TABLE 1

Aryl Substituted "Anilines"

Figure 5:
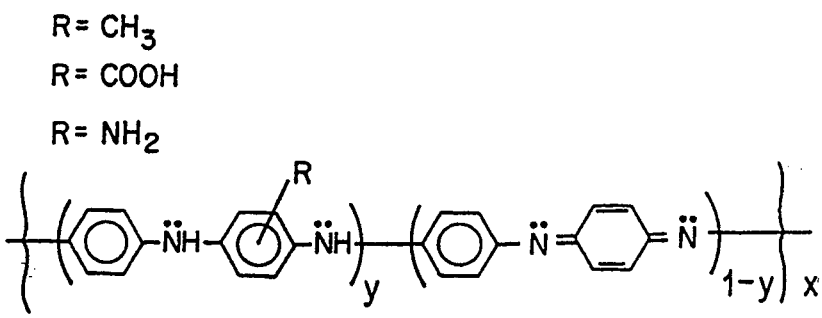
FIG. 5 represents general structural formulae of polyaniline with aryl substituents.

2-amino-6-methylbenzoic acid
2-amino-3-methylbenzoic acid
3,5-diaminobenzoic acid
o-aminobenzoic acid
m-aminobenzoic acid
m-phenylenediamine The resulting polymer is expected to have the general structural formulae shown in FIG. 5 where R=—COOH, —NH$_2$, —CH$_3$.

EXAMPLE 7

Surface Chemical Modifications Of Supported, Electrosynthesized, Polyaniline Film An electrode-supported, polyaniline film prepared as in Example 5 above was immersed in 1:1 mixed acid of sulphuric:nitric acid for 30 seconds. The electrode was withdrawn and the film was then rinsed in 2.0 M HCl. This treatment results in electrophilic aromatic substitution at the phenylene ring of the preformed polymer backbone and in this case introduces aryl nitro groups. The treated film was then immersed in a room temperature solution of aqueous stannous chloride for four minutes. Treatment of the surface modified polyaniline film with stannous chloride results in conversion of the aromatic nitro groups to free primary amines. The result is a surface modified polyaniline film in which there are aryl amine substituents as shown in FIG. 5 for which R=—NH$_2$.

EXAMPLE 8

Figure 7:
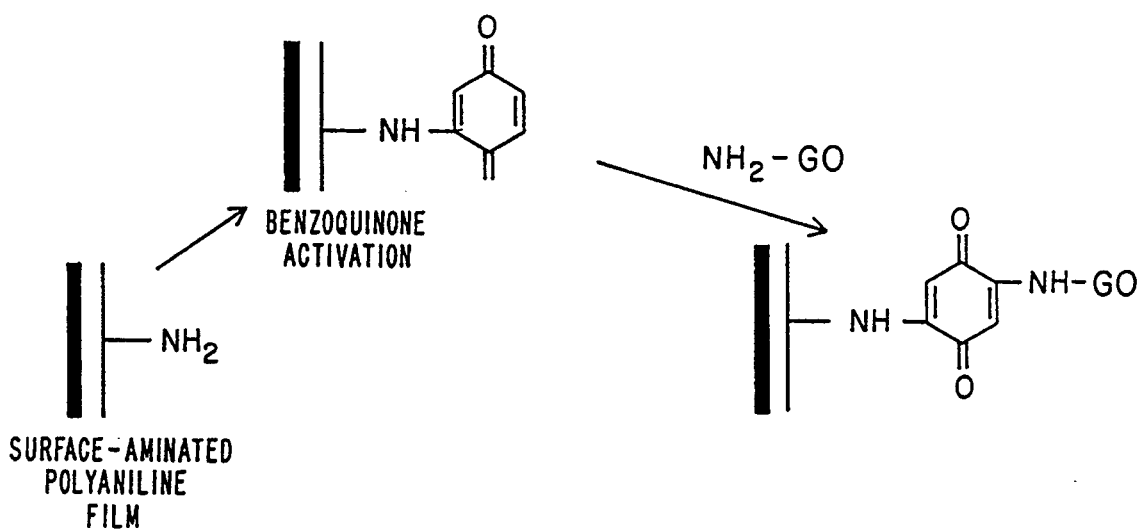
FIG. 7 is a schematic illustration of a reaction of a linking agent with a surface modified polyaniline film and the subsequent immobilization of an enzyme on the surface modified polyaniline film in accordance with the invention.
Figure 6:
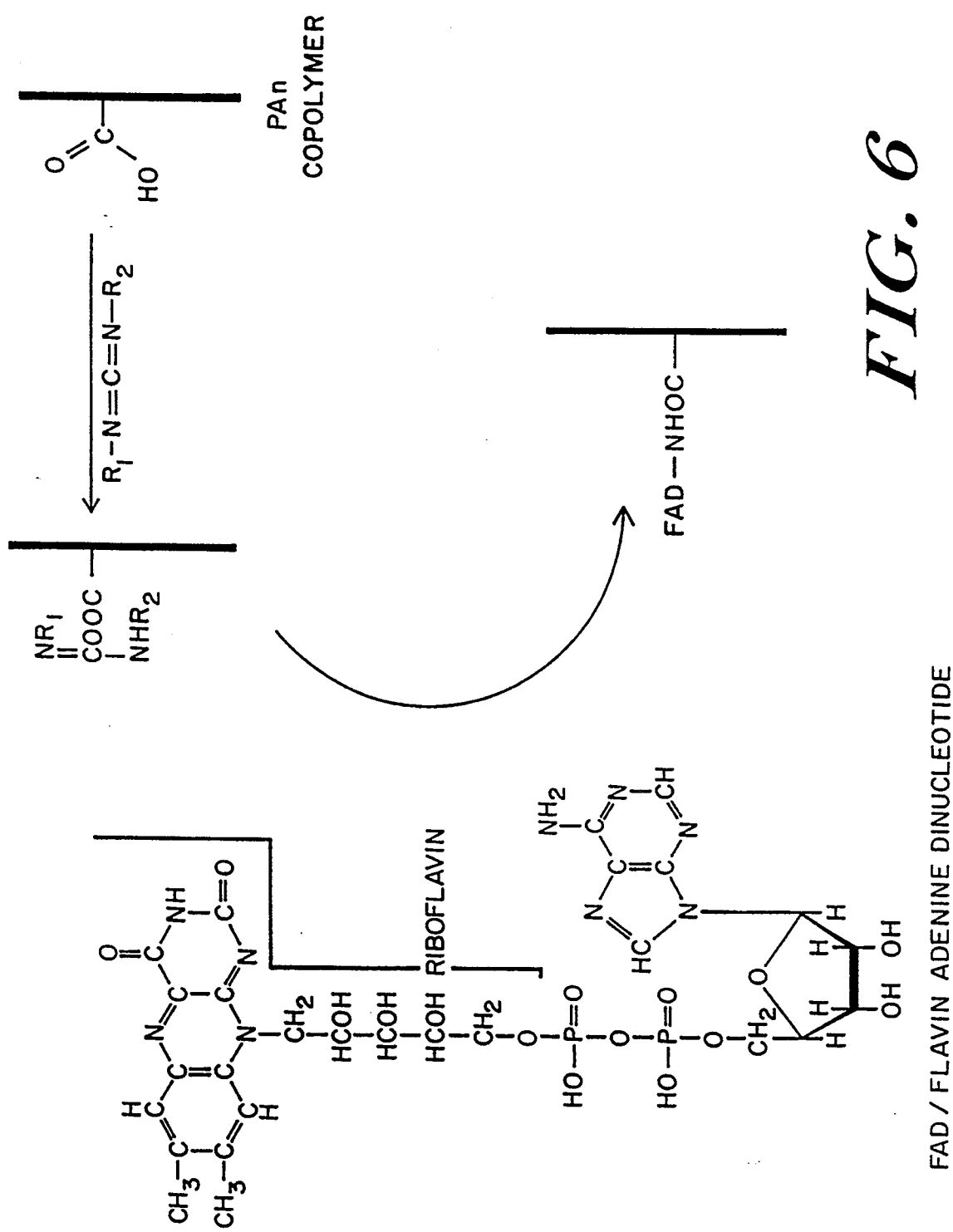
FIG. 6 is a schematic illustration of a FAD derivatized polyaniline surface according to the invention.

Specific Immobilization Of The Bioactive, Enzyme Cofactor, Flavin Adenine Dinucleotide (FAD) To The Surface Of The Chemically Modified Polyanilines The aryl carboxylic acid bearing polyaniline copolymer film prepared according to Example 6 above was made to react with the water-soluble carbodiimide, 1-ethyl-3(3-dimethylaminopropyl)-carbodiimide hydrochloride (Pierce Chemicals). Surface available carboxylic acid groups would react with the carbodiimide to yield the surface confined isourea (Mayawaki et al., 838 *Biochemica and Biophysica Acta* 60 (1985)). The electrode supported film was immersed in a 1 mg/ml aqueous, room temperature solution of the carbodiimide for approximately 4 hours. The resulting isourea functionalized surface of the co-polymer film was then rinsed thoroughly in cold, deionized, distilled water before being transferred and immersed in a cold (5° C.) solution of the di-sodium salt of high purity flavin adenine dinucleotide (FAD) (Sigma Chemical Co.) and incubated overnight at 5° C. in a sealed vessel kept in the refrigerator. This reaction yields the FAD derivatized polyaniline surface as a result of coupling through the primary amine of the adenine base of FAD as shown in FIG. 7.

EXAMPLE 9

Specific Immobilization Of The Bioactive Enzyme Glucose Oxidase To The Surface Of The Chemically Modified Polyanilines The surface aryl amine functionalities produced by the above procedures (according to Example 7) were made the sites for the specific immobilization of the enzyme glucose oxidase to the surface of electrode supported polyaniline films. A supported polyaniline film, prepared according to combined Examples 5 and 7 above, was removed from refrigerator storage and immersed in a room temperature saturated solution of p-benzoquincine which was previously prepared in anhydrous 1% isopropyl alcohol in absolute ethanol. After ca. 30 minutes of immersion, the electrode supported film was removed, rinsed in deionized, distilled water then immediately transferred to a cold, pH 7.2, phosphate-buffered saline solution of glucose oxidase (Type VII-S; EC 1.1.3.4 from *Aspergillus niger;* 129,000 units of activity per gram of solid) (Sigma Chemical Co.).

The electrode supported film was allotted to be incubated in the glucose oxidase solution in a sealed container in a refrigerator at 5° C. overnight. Benzoquinone is well known to cause chemical activation of primary amines at surfaces (Brandt et al., 386 *Biochim, Biophys, Acta* 196 (1976)) through formation of the quinone. The surface confined quinone then acts as an effective linking agent between the quinone activated surface and enzyme molecules (Narasimhan et al., 7 *Enzyme Microb, Technol.* 283 (1985)) as shown in FIG. 8.

Following overnight incubation, the electrode-supported, enzyme-modified polyaniline film was removed and tested for immobilized enzyme activity. Use was made of the procedure reported by Wingard, Jr., et al., 748 *Biochim, and Biophys, Acta* 21 (1983).

In the assay procedure, a Bausch & Lomb Spectronic 20 spectrometer was used centered on 460 nm. The unmodified or control film was found to have around 0.8 milliunits of activity per sq. cm, while functionalized and activated film strips were found to have around 75 milliunits of activity per sq. cm. showing clear activation and immobilization of the enzyme.

I claim:

1. A process for the immobilization of an indicator reagent upon a chemically modified surface of an electroactive polymeric substrate having a predetermined electrical conductivity, the process comprising:
   (a) reacting an electroactive polymeric substrate selected from the group consisting of polyacetylene, polypyrrole, polyaniline and polythiophene with at least one chemical modification reagent to produce an activated surface containing new functional groups capable of covalent bonding on the surface of the substrate, the activated surface being associated with a predetermined electrical conductivity;
   (b) reacting the activated surface on the substrate with a linking agent; and
   (c) reacting the linking agent with an indicator reagent to covalently band the indicator reagent to the activated surface of the substrate such that the predetermined electrical conductivity of the substrate can be altered by reactions of an analyte with the indicator reagent.

2. The process of claim 1 wherein the electroactive polymer is polyacetylene and the method of surface activation comprises the formation of surface hydroxyl groups.

3. The process of claim 1 wherein the electroactive polymer is polyacetylene and the linking agent is p-benzoquinone.

4. The process of claim 3 wherein the indicator reagent is glucose oxidase.

5. The process of claim 1 wherein the electroactive polymer is polyanaline and the method of surface activation comprises immersion of the polymer in a mixed sulphuric:nitric acid solution and said activated surface comprises amino groups.

6. The process of claim 1 wherein the electroactive polymer polyanaline and the linking agent is carbodiimide.

7. The process of claim 6 wherein the indicator reagent is flavin adenine dinucleotide.

8. The process of claim 1 wherein the electroactive polymer is polyanaline and the linking agent is p-benzoquinone.

9. The process of claim 8 wherein the indicator reagent glucose oxidase.

10. A method for detecting the presence of an analyte in a sample comprising contacting a sample with a material comprising an electroactive polymeric substrate having a predetermined electrical conductivity containing a covalently bound indicator reagent, reacting analyte in the sample with the indicator reagent to change the electrical conductivity of the suffererate and from the change in the electrical conductivity determining the presence of the analyte, said material being prepared by reacting an electroactive polymeric substrate selected from the group consisting of polyacetylene, polypyrrole, polyaniline and polythiophene having a predetermined electrical conductivity at least one chemical modification reagent to produce an activated surface containing new functional groups capable of covalent bonding on the surface of the substrate and having a predetermined electrical conductivity, and reacting the new functional groups of the activated surface with an indicator reagent to covalently bond the indicator reagent to the surface of the substrate.

11. A material comprising; an electroactive polymeric substrate containing a covalently bound indicator reagent, said material being prepared by reacting an electroactive polymeric substrate selected from the group consisting of polyacetylene, polypyrrole, polyaniline and polythiophene having a predetermined electrical conductivity with at least one chemical modification reagent to produce an activated surface on the substrate containing new functional groups capable of covalent bonding on the surface of said substrate and said activated surface having a predetermined electrical conductivity, reacting said activated surface with a linking agent, and reacting the linking agent with an indicator reagent to covalently bond the indicator reagent to the activated surface of said substrate, whereby the predetermined electrical conductivity of the substrate can be altered by reactions of an analyte with the indicator reagent.

* * * * *